United States Patent
Schwartz et al.

(10) Patent No.: US 9,833,165 B2
(45) Date of Patent: Dec. 5, 2017

(54) CHECKING FOR PERFORATION OF THE EPICARDIUM USING MAGNETIC RESONANCE IMAGING

(71) Applicant: BIOSENSE WEBSTER (ISRAEL) LTD., Yokneam (IL)

(72) Inventors: Yitzhack Schwartz, Haifa (IL); Assaf Govari, Haifa (IL); Vadim Gliner, Haifa (IL)

(73) Assignee: Biosense Webster (ISRAEL) Ltd., Yokneam (IL)

( * ) Notice: Subject to any disclaimer, the term of this patent is extended or adjusted under 35 U.S.C. 154(b) by 514 days.

(21) Appl. No.: 14/264,532

(22) Filed: Apr. 29, 2014

(65) Prior Publication Data

US 2015/0305646 A1    Oct. 29, 2015

(51) Int. Cl.
| | |
|---|---|
| A61B 5/055 | (2006.01) |
| A61B 18/14 | (2006.01) |
| A61B 5/107 | (2006.01) |
| A61B 5/00 | (2006.01) |
| A61B 5/0402 | (2006.01) |
| A61B 90/00 | (2016.01) |

(52) U.S. Cl.
CPC .............. *A61B 5/055* (2013.01); *A61B 5/1075* (2013.01); *A61B 5/4836* (2013.01); *A61B 18/1492* (2013.01); *A61B 5/0402* (2013.01); *A61B 2090/374* (2016.02)

(58) Field of Classification Search
CPC .......... A61B 18/1492; A61B 2090/374; A61B 5/0402; A61B 5/055; A61B 5/1075; A61B 5/4836
See application file for complete search history.

(56) References Cited

U.S. PATENT DOCUMENTS

| | | | |
|---|---|---|---|
| 5,620,479 A | * | 4/1997 | Diederich .............. A61B 18/18 601/3 |
| 6,226,542 B1 | | 5/2001 | Reisfeld |
| 6,301,496 B1 | | 10/2001 | Reisfeld |
| 6,695,808 B2 | | 2/2004 | Tom |
| 6,814,733 B2 | | 11/2004 | Schwartz |
| 6,892,091 B1 | | 5/2005 | Ben Haim |
| 6,997,924 B2 | | 2/2006 | Schwartz |
| 7,156,816 B2 | | 1/2007 | Schwartz |
| 7,536,218 B2 | | 5/2009 | Govari |
| 7,753,576 B2 | | 7/2010 | Marcinkewicz |
| 8,078,259 B2 | | 12/2011 | Prince |

(Continued)

FOREIGN PATENT DOCUMENTS

WO    WO 2010/144402 A2    12/2010

OTHER PUBLICATIONS

U.S. Appl. No. 13/589,347, filed Aug. 20, 2012.

(Continued)

*Primary Examiner* — Ruth S Smith
(74) *Attorney, Agent, or Firm* — Louis J. Capezzuto (57) ABSTRACT

Cardiac ablation is monitored to detect hemopericardium by iteratively acquiring magnetic resonance imaging (MRI) data that includes the pericardium, measuring the pericardium by analyzing the sets of MRI data, making a determination that a measurement of the pericardium in consecutive sets of MRI data differ, and responsively to the determination reporting a change in configuration of the pericardium.

18 Claims, 5 Drawing Sheets

(56) References Cited

U.S. PATENT DOCUMENTS

| | | |
|---|---|---|
| 2007/0078325 A1 | 4/2007 | Fuimaono et al. |
| 2010/0280357 A1 | 11/2010 | Bi et al. |
| 2010/0317961 A1* | 12/2010 | Jenkins .................. A61B 5/055 600/411 |
| 2011/0071384 A1 | 3/2011 | Kimura |
| 2013/0172875 A1 | 7/2013 | Govari |
| 2014/0081125 A1 | 3/2014 | Zhou et al. |
| 2015/0327805 A1* | 11/2015 | Ben-Haim ............. A61B 6/037 600/411 |

OTHER PUBLICATIONS

Hoey, Edward T.D. et al.: Sinus of Valsalva Aneurysms: Assessment With Cardiovascular MRI. Cardiopulmonary Imaging, AJR:194, Jun. 2010, pp. 495-504.

Lang, Nora et al.: A Blood-Resistant Surgical Glue for Minimally Invasive Repair of Vessels and Heart Defects. Science Translational Medicine, Jan. 8, 2014, vol. 6, Issue 218, pp. 1-10.

Rajiah, Prabhakar: Cardiac MRI:Part 2, Pericardial Diseases. AJR:197, Oct. 2011, pp. 621-634.

Koktzoglou, I. et al., "Diffusion-prepared segmented steady-state free precession: Application to 3D black-blood cardiovascular magnetic resonance fo the thoracic aorta and carotid artery walls", Journal of Cardiovascular Magnetic Resonance, Dekker, New York, NY, US. vol. 9, No. 1, Jan. 1, 2007, pp. 33-42.

\* cited by examiner

CHECKING FOR PERFORATION OF THE EPICARDIUM USING MAGNETIC RESONANCE IMAGING

BACKGROUND OF THE INVENTION

Field of the Invention

This invention relates to cardiac catheterization. More particularly, this invention relates to improvements in detecting complications of cardiac catheterization.

Description of the Related Art

The meanings of certain acronyms and abbreviations used herein are given in Table 1.

TABLE 1

Acronyms and Abbreviations

| MRI | Magnetic Resonance Imaging |
| --- | --- |
| ECG | Electrocardiogram |

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating such arrhythmias include surgically disrupting the origin of the signals causing the arrhythmia, as well as disrupting the conducting pathway for such signals. By selectively ablating cardiac tissue by application of energy via a catheter, it is sometimes possible to interrupt or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy while avoiding excessive contact force that might cause damage to the cardiac tissues. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

In an invasive procedure performed on the heart, particularly a procedure involving mapping and ablation, there is a concern that the myocardial wall may be perforated, leading to unwanted entry of blood into the pericardial sac (hemopericardium) and development of a life threatening cardiac tamponade. Such a perforation is typically small. However, the flow rate of blood from the ventricular or atrial chamber into the pericardial space varies from low to high. Accordingly, it may take from a few minutes to a number of hours before the existence of the perforation is apparent.

A detailed description of the pericardial anatomy is given in the document *Cardiac MRI: Part 2, Pericardial Diseases*, Prabhakar Rajiah, American Journal of Roentgenology. October 2011; Vol. 197:W621-W634 (Rajiah), which is herein incorporated by reference. As is explained in Rajiah, the so-called "black blood" magnetic resonance imaging (MRI) technique may include weighted T1 and T2 sequences. The technique is useful to visualize normal pericardial anatomy, as well as effusions of blood into the pericardial sac. The black blood technique is a spin-echo MRI mode, in which high-velocity signal loss occurs. The technique employs excitation and refocusing pulses, which are 90° out of phase. Blood flowing within the heart in a slice of interest at the time of the 180° pulse will not have received the 90° pulse. Therefore, there is no magnetization in the transverse plane of the slice to refocus to an echo, and only a dark area appears on the resulting image. Pericardial fluid, which is not in rapid motion, appears as a white band on the image.

SUMMARY OF THE INVENTION

Embodiments of the present invention operate the black blood MRI protocol as a computer process in order to detect real-time perforation of the myocardial wall during an ongoing cardiac catheterization procedure. Typically, MRI and ablation are performed concurrently using a combined, MRI and CARTO electroanatomical mapping system, or suite. In order to detect perforation, an image-processing program is operated periodically in background on black blood imaging data. The computer processor runs an automatic image-processing algorithm that compares successive images in order to detect changes in the anatomy of the pericardium. The images may be analyzed by the processor without the images being actually displayed. Alternatively or additionally, the processor may run the black blood protocol in background when perforation is suspected, for example, after a specific predefined contact force was exceeded during catheter manipulation, mapping or an ablation.

In some embodiments the processor is configured to check specific susceptible regions of the pericardium, where there is an expectation that blood is most likely to start accumulating.

The black blood protocol as described herein allows nearly instantaneous intraoperative detection of perforation of the epicardium. Its automatic mode of operation is transparent to the operator, and does not interfere with the ongoing catheterization procedure unless an abnormal event is detected.

There is provided according to embodiments of the invention a method, which is carried out by inserting a probe into a heart of a living subject, navigating the probe into a contacting relationship with a target tissue of the heart, and performing a medical procedure on the target. The method is further carried out during the medical procedure by iteratively acquiring magnetic resonance imaging (MRI) data that includes the pericardium, including a first set of MRI data and a second set of MRI data, measuring the pericardium by analyzing the sets of MRI data, making a determination that a measurement of the pericardium in the second set of MRI data differs from the measurement of the pericardium in the first set of MRI data, and responsively to the determination reporting a change in configuration of the pericardium.

According to an aspect of the method, acquiring the MRI data comprises black blood imaging of the pericardium.

According to still another aspect of the method, measuring the pericardium comprises detecting a separation of the visceral layer from the parietal layer of the pericardium.

According to another aspect of the method, making the determination comprises failing to detect the separation on the first set of MRI data and detecting the separation on the second set of MRI data.

According to one aspect of the method, making the determination comprises detecting a change in a distance between the visceral layer and the parietal layer that exceeds a predetermined value, which can be 0.1 mm.

According to still another aspect of the method, the separation is detected in a superior recess of the pericardium, adjacent to a posterolateral wall of the heart or adjacent to an inferolateral right ventricular wall of the heart.

According to yet another aspect of the method, iteratively acquiring is performed at intervals of between 5 sec and 3 minutes.

There is further provided according to embodiments of the invention a medical apparatus, including a probe, adapted for insertion into a heart, a memory having programs stored therein, a display, and a processor linked to the display and coupled to access the memory to execute the programs. The processor is connectable to a MRI apparatus. The programs include a MRI control module and an image analysis module, wherein the programs cause the processor to perform the steps of iteratively acquiring magnetic resonance imaging (MRI) data that includes the pericardium by invoking the MRI control module to communicate control signals to the MRI apparatus. The MRI data includes a first set of MRI data and a second set of MRI data. The processor is operative for measuring the pericardium by analyzing the sets of MRI data using the image analysis module, making a determination that a measurement of the pericardium in the second set of MRI data differs from the measurement of the pericardium in the first set of MRI data, and responsively to the determination reporting a change in configuration of the pericardium, wherein iteratively acquiring, measuring, making a determination, and reporting are performed while performing a medical procedure on a living subject.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as USB memory, hard drive, electronic media or CD-ROM. The code may be distributed on such media, or may be distributed to users from the memory or storage of one computer system over a network of some type to storage devices on other computer systems for use by users of such other systems.

Figure 1:
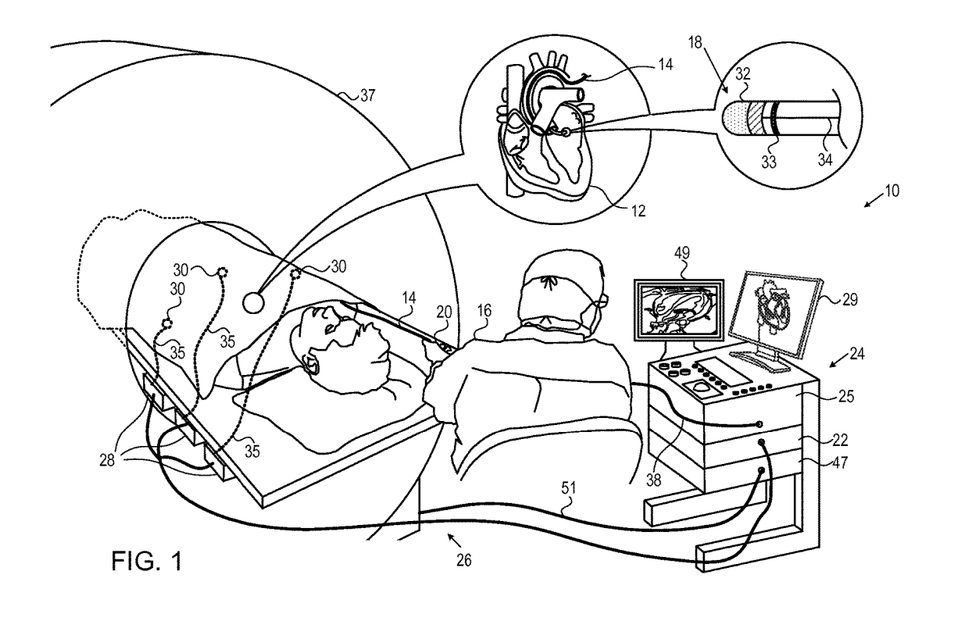
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for performing catheterization procedures on a heart 12 of a living subject, which is constructed and operative in accordance with a disclosed embodiment of the invention. The system 10 typically comprises a general purpose or embedded computer processor, which is programmed with suitable software for carrying out the functions described hereinbelow. Thus, although portions of the system 10 shown in FIG. 1 and other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. Alternatively or additionally, the system 10 may comprise a digital signal processor or hard-wired logic.

The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 22 located in a console 24, according to the methods disclosed in U.S. Pat. Nos. 6,226, 542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765, which is capable of producing electroanatomic maps of the heart as required for the ablation. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating (or cooling) it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and/or one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power connections. The catheter 14 may be adapted to conduct ablative energy to the heart using any known ablation technique, e.g., radiofrequency energy, ultrasound energy, freezing technique and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

A MRI imaging device 37 is linked to a control processor 47, which may be located in the console 24. An operator may select or override automatic operation to control the operation of the MRI imaging device 37, for example by revising imaging parameters. The control processor 47 may communicate with the MRI imaging device 37 via a cable 51 to enable and disable the MRI imaging device 37 to acquire image data. An optional display monitor 49, linked to the control processor 47, allows the operator to view images produced by the MRI imaging device 37. When the display monitor 49 is not included, the images may still be viewed on a monitor 29, either via a split screen or in alternation with other images.

As noted above, the catheter 14 is coupled to the console 24, which enables the operator 16 to observe and regulate the functions of the catheter 14. The processor 22 is typically a computer with appropriate signal processing circuits. The processor 22 is coupled to drive the monitor 29. The signal processing circuits typically receive, amplify, filter and digitize signals from the catheter 14 and the MRI imaging device 37, including signals generated by the above-noted sensors and a plurality of location sensing electrodes (not shown) located distally in the catheter 14. The digitized signals are received and used by the console 24 and the positioning system to compute the position and orientation of the catheter 14, analyze the electrical signals from the electrodes and generate desired electroanatomic maps. The above-described arrangement works well when a shared coordinate system is shared between system components, e.g., a combined CARTO-MRI system. This is especially true when ablating the atria, as its wall is very thin, and it is necessary to define its boundaries. Despite advances in image processing, edge detection of the endocardial wall continues to be challenging, and conventionally requires manual analysis of sequential slice images. However, with a trackable, MRI-compatible, indwelling catheter that touches the endocardial wall and measures contact-force, manual analysis can be avoided.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally placed catheter, which is inserted into the heart 12 maintained in a fixed position relative to the heart 12. Conventional pumps and lines for circulating liquids through the catheter 14 for cooling the ablation site are provided.

Figure 2:
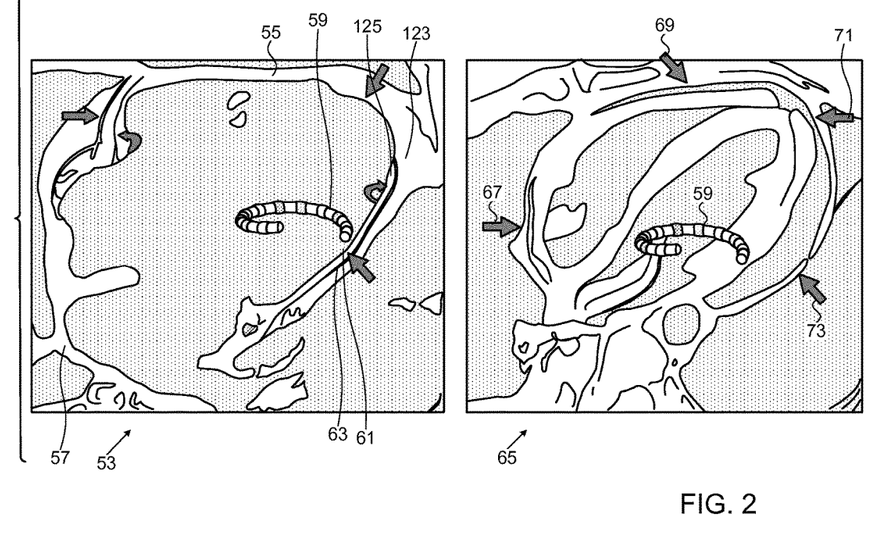
FIG. 2 shows MRI images illustrating discovery of pericardial fluid in accordance with an embodiment of the invention.

Reference is now made to FIG. 2, which shows MRI images illustrating discovery of pericardial fluid in accordance with an embodiment of the invention. At the left side of the figure is a black blood intraoperative MRI frame 53 showing a four-chamber view of a normal heart 55 and pericardium 57. The distal portion of a cardiac catheter 59 is shown in contact with endocardial surface 61 of the heart 55. A relatively small amount of fluid in the pericardial space appears as a narrow black band 63 lying between thicker white strips 123, 125. The strips 123, 125 correspond to the parietal and visceral pericardium, which are often inseparable on images of this sort. In FIG. 2 the two pericardial layers can be resolved as a result of a physiologic amount of pericardial fluid.

At the right of FIG. 2 is a diagram comprising another intraoperative black blood MRI frame 65 with the cardiac catheter 59 superimposed thereon. Blood has accumulated within the pericardium, presumably originating from the cardiac chamber. If the MRI frame 65 were presented visually, as shown in FIG. 1, the operator would recognize the hemopericardium as an intraoperative complication of the catheterization. Alternatively, the control processor 47 would have acquired successive MRI frames, and would have identified the MRI frame 65 as significantly deviating from previous frames, e.g., the MRI frame 53. In FIG. 2, a hemorrhagic pericardial effusion has occurred as a complication of cardiac catheterization. The blood appears on the MRI frame 65 as a region of low signal intensity, indicated by arrows 67, 69, 71, 73. Typically, the earliest collection of pericardial fluid occurs adjacent to the posterolateral left ventricular wall or the inferolateral right ventricular wall, after which pericardial fluid accumulates in the superior recess.

Figure 3:
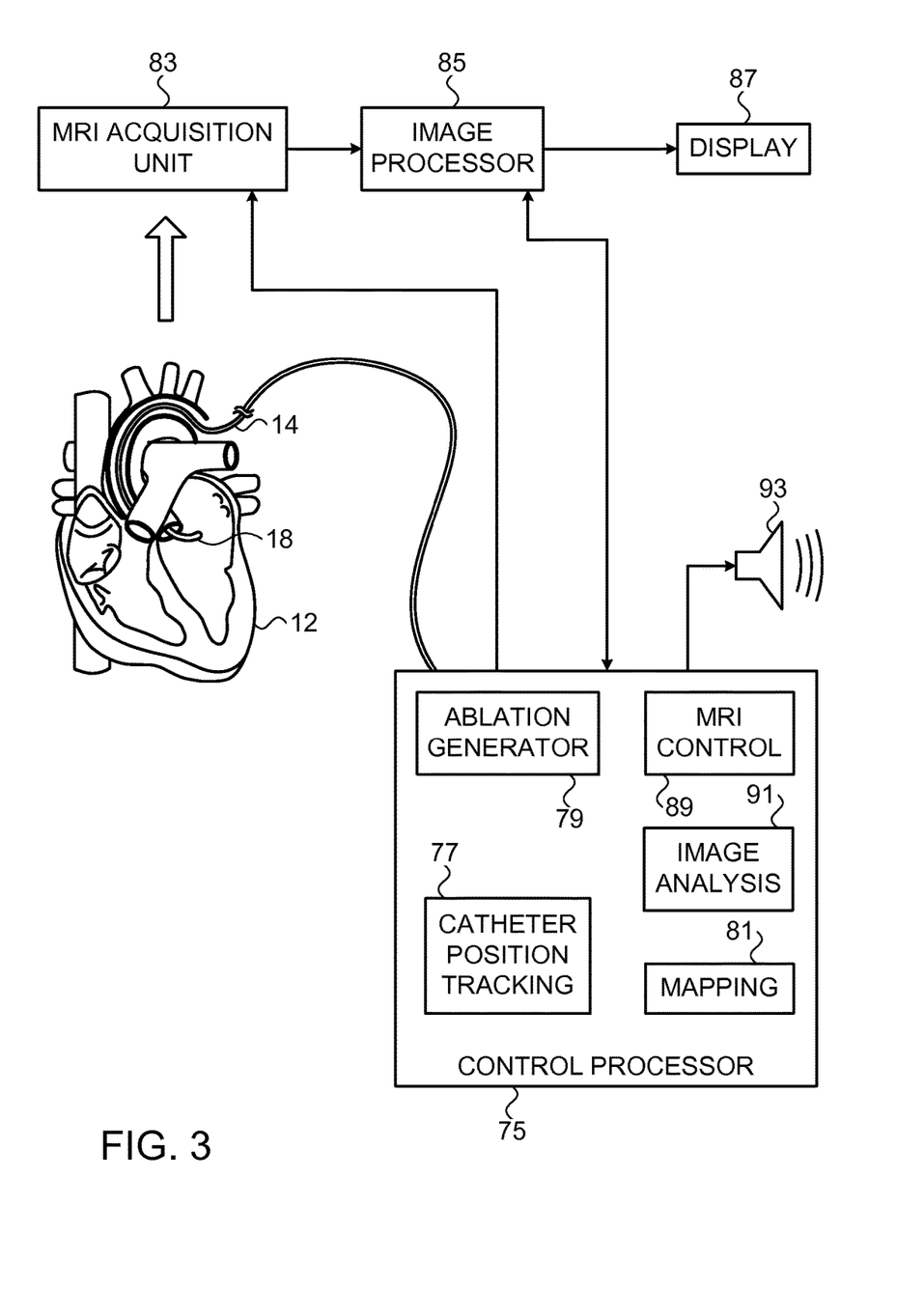
FIG. 3 is a pictorial block diagram of an embodiment of the system shown in FIG. 1, in accordance with an embodiment of the invention.

Reference is now made to FIG. 3, which is a pictorial block diagram of an embodiment of the system 10 (FIG. 1) for detecting perforation of the epicardium during cardiac catheterization using magnetic resonance imaging, in accordance with an embodiment of the invention. A control processor 75 communicates with catheter 14 while it is in the heart 12 via cable 51 and deals with routine aspects of a medical procedure involving the catheter 14, using any of a position tracking position tracking module 77, an ablation generator 79 and a mapping module 81. MRI acquisition unit 83 may be activated from time to time by the operator to acquire and prepare MRI images using the facilities of an image processor 85 and a display 87 to assist the operator in visualizing the cardiac anatomy and optionally visualizing the distal portion of the catheter 14 in embodiments in which sensing elements appropriate to MRI techniques are included with the catheter 14. In addition, a MRI control program 89 executing in the control processor 75 transmits control signals to the MRI acquisition unit 83 causing MRI images to be acquired by the MRI acquisition unit 83 according to a predefined schedule or responsively to calculations of an image analysis module 91, which operates on data obtained from the image processor 85. The image processor 85 may be provided in the MRI acquisition unit 83, or may be integral with the control processor 75, or be a separate entity as shown in FIG. 3. As is explained in further detail below, the image analysis module 91 is programmed to detect an increase in the volume of the pericardial space during the course of the catheterization, and when conditions are met, to alert the operator by a notification on the display 87, audibly via a speaker 93, or both.

Figure 4:
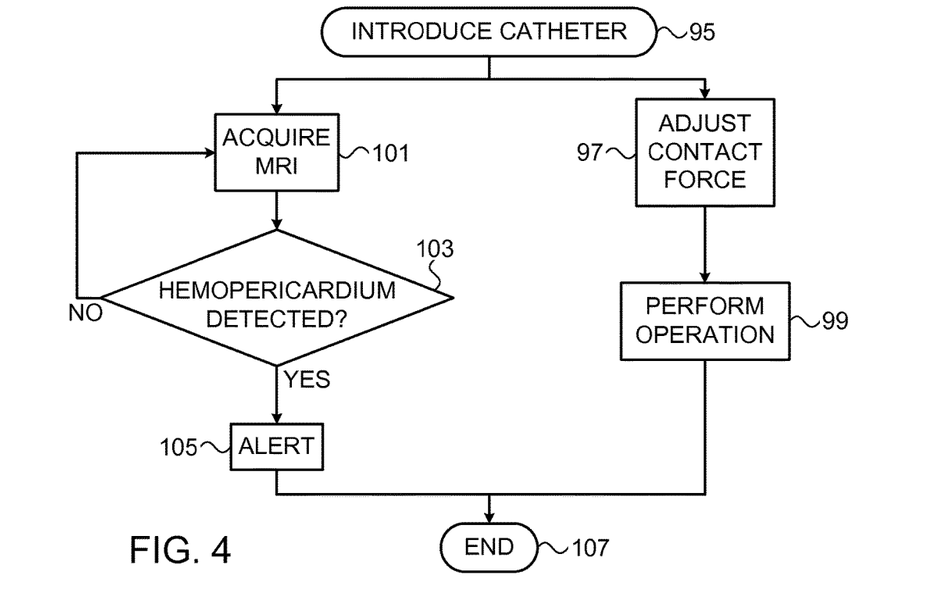
FIG. 4 is a flow-chart of a method of evaluating the pericardium during cardiac catheterization, in accordance with an embodiment of the invention.

Reference is now made to FIG. 4, which is a flow-chart of a method of evaluating the pericardium during cardiac catheterization, in accordance with an embodiment of the invention. At initial step 95, a cardiac catheter is introduced into a subject and navigated to a target, typically within a chamber of the heart. This may be accomplished using the facilities of the above-mentioned CARTO system, optionally aided by an imaging modality, e.g., MRI.

Next, at an optional step 97, contact between the catheter and the target is verified and the contact force adjusted if necessary. Contact force determination can be accomplished using the teachings of application Ser. No. 13/589,347, entitled "Machine Learning in Determining Catheter Electrode Contact" and U.S. Patent Application Publication No. 2013/0172875, entitled "Contact Assessment Based on Phase Measurement", both of which are commonly assigned and are herein incorporated by reference.

At step 99, a medical operation is carried out by the operator, e.g., mapping or ablation at an area of interest.

During the performance of steps 97, 99 an iterative procedure involving MRI is carried out:

An MRI image of the field of interest is acquired at step 101, and analyzed to evaluate the configuration of the pericardial space. The first iteration of step 101 constitutes a reference against which image data from subsequent iterations are compared.

Next, at decision step 103, it is determined if analysis of the image data shows increased separation between the parietal and visceral pericardium in at least a portion of the pericardial space, indicating the formation of a hemopericardium. Width of the pericardial sac is an exemplary indication of the volume of the pericardial sac, and hence its liquid content. Other indicators of pericardial volume that can be determined on MRI images will occur to those skilled in the art. In some embodiments, the analysis may be accomplished with the aid of a conventional image processing program provided by the manufacturer of the MRI imaging device, optionally supplemented by the image analysis module 91 (FIG. 3). Alternatively, the image analysis module 91 may be programmed to evaluate raw or partially processed image data so as to recognize any intraoperative change in the pericardial anatomy, for example, in a comparison of the parietal and visceral pericardial layers in the two images in FIG. 2. One set of images is compared with a baseline set or a previous performance of decision step 103. In any case, the evaluation of the image data is performed automatically, and may be executed as a background process by the control processor 75 (FIG. 3). If the determination at decision step 103 is negative, then after a predetermined delay interval control returns to step 101 for acquisition of new image data.

If the determination at decision step 103 is affirmative then control proceeds to step 105. An alert to the operator is issued.

Final step 107 is performed upon completion of step 99 or step 105, whichever occurs first. The procedure accordingly terminates normally or abnormally.

Figure 5:
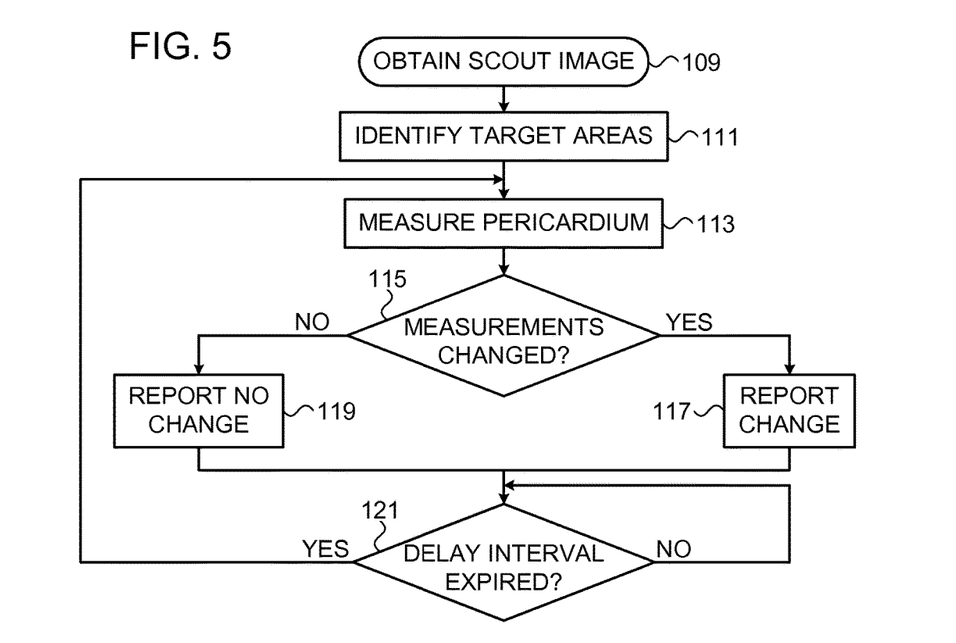
FIG. 5 is a detailed flow-chart illustrating details of the method shown in FIG. 4, in accordance with an embodiment of the invention.

Reference is now made to FIG. 5, which is a flow-chart illustrating details of decision step 103 (FIG. 4), in accordance with an embodiment of the invention. Normal pericardial thickness ranges from 1.2 to 1.7 mm on MRI images. When fluid accumulates in the pericardium quickly, pericardial pressures can increase substantially and produce well-known hemodynamic effects. One method of automatically evaluating MRI image data of the heart and pericardium in successive iterations of decision step 103 (FIG. 4) exploits information known from the above-noted Rajiah document: pericardial fluid does not necessarily spread homogeneously. Rather, the earliest collection of pericardial fluid occurs adjacent to the posterolateral left ventricular wall or the inferolateral right ventricle wall, after which pericardial fluid accumulates in the superior recess. Moderate-sized collections of fluid (100-500 mL) tend to accumulate in the anterior aspect of the right ventricle as well. Large effusions are seen anterior to the right atrium and right ventricle.

At initial step 109, a baseline or scout MRI image of the heart and pericardium is obtained. This may be conveniently done at the beginning of the catheterization session, or may be a previously obtained image. The images described in this method are obtained using the above-noted black blood technique.

Next, at step 111 the following target areas are identified: the posterolateral left ventricular wall, the inferolateral right ventricle wall, and the superior recess.

Next, at step 113, MRI images are acquired to include at least the target areas that were identified in step 111. In some embodiments, the images are selected or acquired to synchronize with cardiorespiratory motions. Measurements of the distances between the visceral and parietal pericardium are recorded at the target areas. This may be accomplished using routines provided by the image analysis module 91 (FIG. 3). The measurements may include defining spatial regions of interest for the posterolateral left ventricular wall, and the inferolateral right ventricular wall, and analyzing the data in the regions of interest, respectively.

Next, at decision step 115, it is determined if the measurements obtained in step 113 vary from a previous iteration (or the scout image) by more than a predetermined value. A suitable threshold of variation for this purpose depends upon the strength of the MRI magnetic field and is 0.1-0.3 mm for 3 T and 1.5 T, respectively. It will be recalled from the discussion above that normally almost no separation is evident between the parietal and visceral and visceral layers of the pericardium on black blood MRI images. However, in some patients, there is a very small physiological pericardial effusion, which represents a normal anatomical variant. Appearance of any discernable separation on a new iteration of step 113 when it was not detectable on a previous iteration may be a significant change in the images.

If the determination is affirmative, then an alert is reported at step 117. Otherwise, a negative report is communicated at step 119.

After performing either of steps 117, 119, delay step 121 is performed. The delay interval is not critical, but should be small enough to detect significant changes in the pericardium before hemodynamic changes occur. A delay interval of 5 seconds is suitable. However, longer delay intervals may be tolerated, and the intervals may vary in different phases of the medical procedure. For example during ablation, the intervals may be shortened, while during mapping longer intervals may be chosen. Thereafter, a new iteration begins at step 113.

Figure 6:
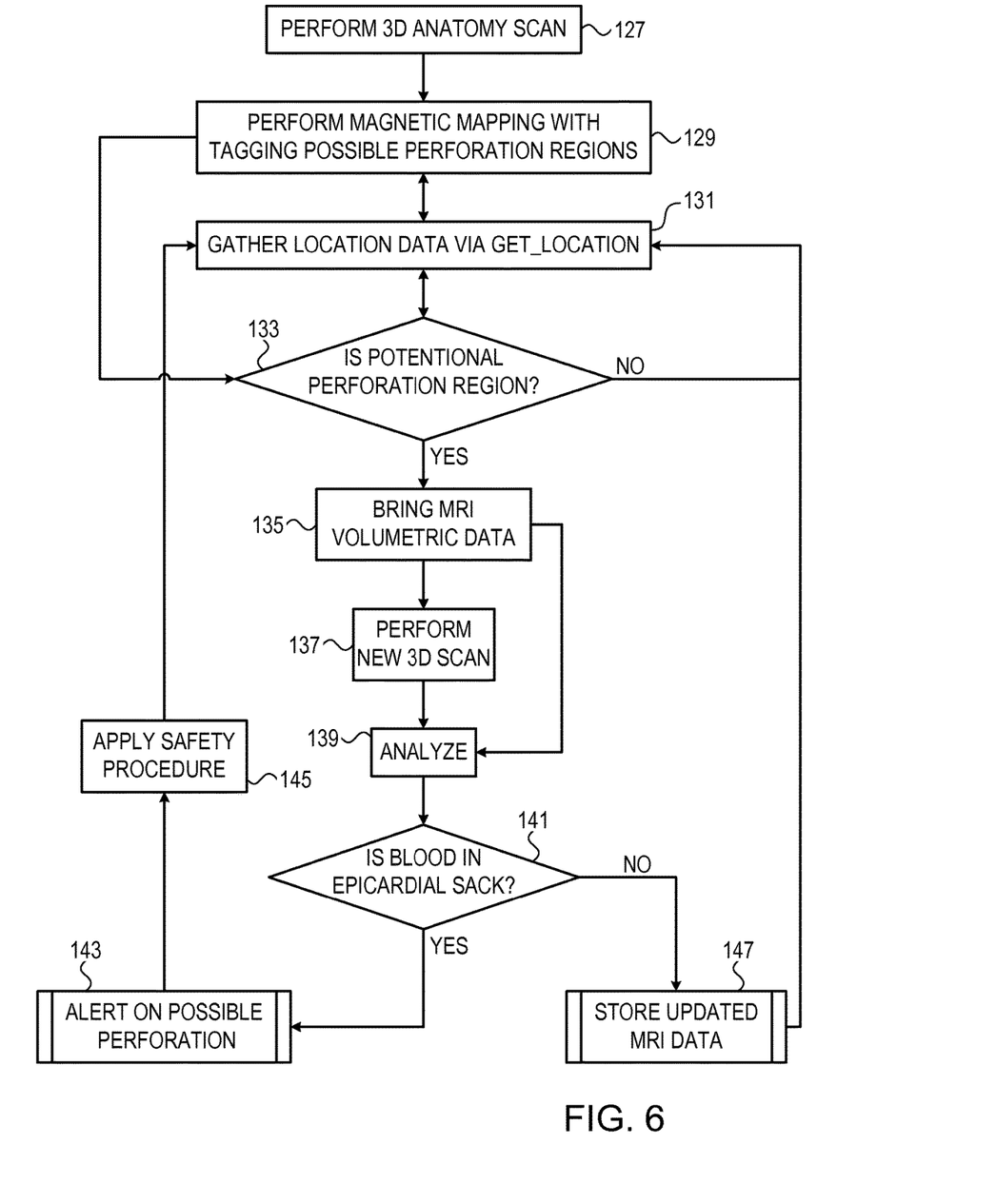
FIG. 6 is a detailed flow chart of a method of automatic detection of hemopericardium, in accordance with an embodiment of the invention.

Reference is now made to FIG. 6, which is a detailed flow chart of a method of automatic detection of hemopericardium, in accordance with an embodiment of the invention. The steps shown in FIG. 6 are discussed with reference to the following pseudocode, and represent computer-implemented functions.

Step 127: V]=Perform_3D_Anatomy_Scan(x0,y0,z0, size_X,size_Y,size_Z,O). This function receives coordinates, orientation and image size and performs a 3D volumetric scan. The scan can be rendered also as a 2D scan.

Step 129 [M]=Perform_Magnetic_Mapping_with_tagging_possible_perforation_regions (x,y,z,is_dangerous). This function receives coordinates, and a Boolean parameter if the current region is dangerous or not and returns a value M, which is binary 3D mask of 1 for dangerous pixels and 0 otherwise.

Tagging can be manually pre-defined or performed in real time according to the following criteria:
Mode==1: Pre-defined manually
Mode==2: if current_tissue_thickness>former_tissue_thickness
Mode==3: Contact_Force_value>threshold_CF
Mode==4: Blood_Pressure<threshold_BP
Mode==5: Is_Abnormal_Ablation_Parameter_exist Step 131 [L,O]=Get_Location (B1,B2,B3). This function returns catheter position and orientation relative to MRI system of coordinates according to a magnetic field B received from the location pad.

Decision step 133 [is_true]=Is_potential_perforation_region(L,O,M). This function receives a mask (3D volumetric binary data of the mapping and anatomy) and returns Boolean value whether the current location is potential perforation region or not. If the Boolean value is false, step 131 is performed.

If the Boolean value in decision step 133 is true, then step 135 is performed: [Data]=Bring_MRI_volumetric_data(L, O). This function scans quickly a very small region defined by location and orientation via black blood sequence and returns the grey level data.

If conditions are appropriate as noted above, a new 3D scan is performed at step 137

Step 139 represents analysis of the data thus far obtained, and is performed by a group of functions:
[Is_perforated=Analyze(mode) This function receives a mode, which defines which of several analysis types will be applied:
If mode==1 then call Analyze_via_Image_Algebra
Else if mode==2 call Analyze_via_gradient_analysis
Else call Analyze_via_tissue thickness.

Decision step 141 can be performed by invoking one or more of the following functions:
[is_peforated]=Analyze_via_Image_Algebra(Initial,Current).] The ImageAlgebra tool provided by Philips may be used for this function. This function receives an initial volumetric data (from Perform_3D_Anatomy_Scan) as well as current data (from step 135), normalize it by:
Initial=Initial/mean(Initial)
Current=Current/mean(Current)
Apply Image algebra: deviation=abs(Initial-Current)
Max_deviation=max(deviation)
If Max_deviation>threshold→alert.

[is_peforated]=Analyze_via_gradient_analysis(Initial, Current,L,O). Trace a ray from current catheter location, which is in contact with current catheter orientation and derivate the gray level. If there are global minima in the middle, then there is perforation because pericardial sac as well as tissue will provide constant gradient change. But if there is blood (which is black) between the sac and tissue there will be a local minimum (according to Fermat's Law).

[is_peforated]=Analyze_via_tissue thickness (Initial,Current,L,O)
If current_tissue_thickness-initial_tissue_thickness>threshold_TS then is_peforated==true.

Steps 143, 145 concern alerting the operator and taking corrective action, respectively, when a possible or actual perforation is detected at decision step 141. In step 145, the function Apply_Safety_Procedure(is_preforated) disconnects ablation option and may apply lifesaving procedures, which are outside the scope of this disclosure.

If no blood is detected in the pericardial sac at decision step 141, then data is updated and stored at step 147. The algorithm then iterates at step 131.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A computer implemented method for a medical apparatus comprising a probe adapted for insertion into a heart having a pericardium thereabout, the pericardium having a visceral layer and a parietal layer, a memory having the computer implemented method stored therein, a display and a processor linked to the display and a MRI apparatus and being coupled to access the memory to execute the computer implemented method, the computer implemented method comprising the steps of:

acquiring a first set of magnetic resonance imaging (MRI) data from the MRI apparatus that includes the pericardium and subsequently acquiring a second set of MRI data from the MRI apparatus that includes the pericardium;

measuring the pericardium by analyzing the first and second sets of MRI;

making a determination that a measurement of the pericardium in the second set of MRI data differs from the measurement of the pericardium in the first set of MRI data; and responsively to the determination reporting a change in configuration of the pericardium, wherein the steps of acquiring, measuring, making a determination, and reporting are performed while a medical procedure is being performed;

wherein measuring comprises detecting a separation of the visceral layer from the parietal layer of the pericardium and making a determination comprises detecting a change in a distance between the visceral layer and the parietal layer that exceeds a predetermined value.

2. The method according to claim 1, wherein acquiring is performed by black blood imaging of the pericardium.

3. The method according to claim 1, wherein making a determination comprises failing to detect the separation on the first set of MRI data and detecting the separation on the second set of MRI data.

4. The method according to claim 1, wherein the separation is detected in a superior recess of the pericardium.

5. The method according to claim 1, wherein the separation is detected adjacent to a posterolateral wall of the heart.

6. The method according to claim 1, wherein the separation is detected adjacent to an inferolateral right ventricular wall of the heart.

7. The method according to claim 1, wherein the predetermined value is 0.1 mm.

8. The method according to claim 1, wherein acquiring is performed at intervals of between 5 sec and 3 minutes.

9. The method according to claim 1, wherein when it is determined that the measurement of the pericardium in the second set of MRI data differs from the measurement of the pericardium in the first set of MRI data by more than the predetermined value, reporting a change comprises alerting an operator.

10. A medical apparatus, comprising:
a probe, adapted for insertion into a heart, the heart having a pericardium thereabout;
a memory having programs stored therein;
a display; and
a processor linked to the display and being coupled to access the memory to execute the programs, the processor connected to a MRI apparatus, the programs comprising a MRI control module and an image analysis module, wherein the programs cause the processor to perform the steps of:
iteratively acquiring magnetic resonance imaging (MRI) data that includes the pericardium, by invoking the MRI control module to communicate control signals to the MRI apparatus, the MRI data including a first set of MRI data and a subsequently acquired second set of MRI data;
measuring the pericardium by analyzing the first and second sets of MRI data using the image analysis module;
making a determination that a measurement of the pericardium in the second set of MRI data differs from the measurement of the pericardium in the first set of MRI data; and
responsively to the determination reporting a change in configuration of the pericardium, wherein the steps of iteratively acquiring, measuring, making a determination, and reporting are performed while performing a medical procedure on a living subject;
wherein the pericardium has a visceral layer and a parietal layer, wherein measuring comprises detecting a separation of the visceral layer from the parietal layer;
wherein making a determination comprises detecting a change in a distance between the visceral layer and the parietal layer that exceeds a predetermined value.

11. The apparatus according to claim 10, wherein iteratively acquiring is performed by instructing the MRI apparatus to perform black blood imaging of the pericardium.

12. The apparatus according to claim 10, wherein making a determination comprises failing to detect the separation on the first set of MRI data and detecting the separation on the second set of MRI data.

13. The apparatus according to claim 10, wherein the separation is detected in a superior recess of the pericardium.

14. The apparatus according to claim 10, wherein the separation is detected adjacent to a posterolateral wall of the heart.

15. The apparatus according to claim 10, wherein the separation is detected adjacent to an inferolateral right ventricular wall of the heart.

16. The apparatus according to claim 10, wherein the predetermined value is 0.1 mm.

17. The apparatus according to claim 10, wherein iteratively acquiring is performed by controlling the MRI apparatus at intervals of between 5 sec and 3 minutes.

18. The apparatus according to claim 10, wherein when it is determined that the measurement of the pericardium in the second set of MRI data differs from the measurement of the pericardium in the first set of MRI data by more than the predetermined value, reporting a change comprises alerting an operator.

* * * * *